(12) United States Patent
Coppola

(10) Patent No.: US 6,657,074 B1
(45) Date of Patent: Dec. 2, 2003

(54) PROCESS FOR THE PREPARATION OF ACYLATED 1,3-DICARBONYL COMPOUNDS

(75) Inventor: Kevin Coppola, Baton Rouge, LA (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 111 days.

(21) Appl. No.: 10/049,074

(22) PCT Filed: Aug. 8, 2000

(86) PCT No.: PCT/EP00/07710

§ 371 (c)(1),
(2), (4) Date: Feb. 4, 2002

(87) PCT Pub. No.: WO01/10806

PCT Pub. Date: Feb. 15, 2001

Related U.S. Application Data

(63) Continuation-in-part of application No. 09/371,181, filed on Aug. 10, 1999, now abandoned.

(51) Int. Cl.$^7$ .............................................. C07C 69/74
(52) U.S. Cl. ...................................................... 560/126
(58) Field of Search ........................................ 560/126

(56) References Cited

FOREIGN PATENT DOCUMENTS

EP        0 306 996        3/1989

*Primary Examiner*—Paul J. Killos
(74) *Attorney, Agent, or Firm*—Rose M. Allen

(57) ABSTRACT

The present invention relates to a process for preparing acylated 1,3-dicarbonyl compounds by rearrangement of corresponding enol esters. The invention also relates to the preparation of the corresponding tautomer compounds of the acylated 1,3-dicarbonyl compounds.

9 Claims, No Drawings

PROCESS FOR THE PREPARATION OF ACYLATED 1,3-DICARBONYL COMPOUNDS

This application is a continuation-in-part of application Ser. No. 09/371,181 filed Aug. 10, 1999 now abandoned.

FIELD OF THE INVENTION

The present invention relates to process for preparing acylated 1,3-dicarbonyl compounds by rearrangement of corresponding enol esters. The invention also relates to the preparation of the corresponding tautomer compounds of the acylated 1,3-dicarbonyl compounds.

BACKGROUND OF THE INVENTION

The rearrangement of certain enol esters which results in an acylated 1,3-dicarbonyl compounds has been reported in the patent and journal literature wherein certain types catalysts have been disclosed as facilitating the rearrangement reaction. Some of the catalysts that have been disclosed are two molar aluminum chloride, 4-dimethylaminopyridine, aminopyridine derivatives, N-alkylimidazole derivatives, molten sodium acetate, Lewis acid and cyanide source. See U.S. Pat. No. 4,695,653 and references cited and discussed therein.

SUMMARY OF THE INVENTION

Surprisingly, it has now been discovered that an azide catalyst/reagent may be used to facilitate the rearrangement of enol esters to the corresponding acylated 1,3-dicarbonyl compound and/or the corresponding tautomer forms of the acylated 1,3-dicarbonyl compound (future reference to acylated "1,3-dicarbonyl compounds" or other similar descriptors such as "cyclohexanedione derivatives" etc. should be read where appropriate to include the tautomer forms unless otherwise indicated). The acylated 1,3-dicarbonyl compounds produced by the instantly disclosed process are useful themselves as agrochemicals (e.g. pesticides, herbicides, etc.) or may be used as intermediates in the preparation of useful agrochemicals. The azide catalyst/reagent system used in the instant invention has advantages over those previously used. Catalysts such as dimethylaminopyridine must be recovered. Cyanide catalysts and reagents produce hydrogen cyanide which contaminates process streams. The azide catalysts and reagents of the instant invention have the advantage that upon acidification they form hydrozoic acid which decomposes to nitrogen. The instant invention overcomes the need for certain costly catalyst/reagent recovery and waste treatment systems previously associated with the preparation of acylated 1,3-dicarbonyl compounds.

DETAILED DESCRIPTION OF THE INVENTION

One embodiment of the invention is the process for preparing an acylated cyclical 1,3-dicarbonyl compounds or tautomers thereof, comprising the step of rearrangement of the corresponding enol ester, wherein said rearrangement is conducted in the presence of a alkali metal azide. The acylated cyclical 1,3-dicarbonyl compounds are 1,3-cyclohexanediones that are substituted at the 2-position on the cyclohexane ring with an acyl radical. The enol ester compounds that are the starting materials for the process are the O-acyl enol esters of 1,3-cyclohexanediones.

Another aspect of the invention is the process wherein the rearrangement is conducted in the presence of either:

(a) a catalytic amount of an alkali metal azide and a molar excess, with respect to the enol ester, of a base; or
(b) a stoichiometric amount, with respect to the enol ester, of an alkali metal azide and a catalytic amount of a phase-transfer catalyst.

Another embodiment of the invention is the process for preparing the compounds of formula I:

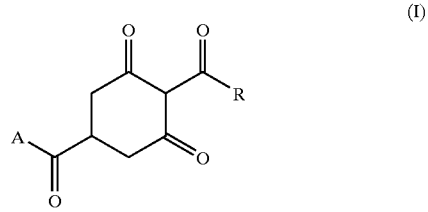

(I)

and tautomers thereof, wherein

R is a group $C_1-C_{10}$ alkyl, $C_3-C_6$ cycloalkyl or phenyl, wherein the phenyl nucleus is unsubstituted or substituted by one to three groups selected from the group consisting of halogen, $C_1-C_4$ alkyl, $C_1-C_4$ alkoxy, $C_1-C_4$ haloalkyl, nitro or cyano; A is $-OR_2$, $-SR_2$ or $-NR_3R_4$ radical;

$R_2$, $R_3$ and $R_4$ are each independently, hydrogen, $C_1-C_6$ alkyl, $C_1-C_6$ haloalkyl, $C_2-C_{10}$ alkoxyalkyl, $C_2-C_{10}$ alkylthioalkyl; $C_3-C_6$ alkenyl which is unsubstituted or substituted by halogen, $C_1-C_4$ alkoxy or $C_1-C_4$ alkylthio; $C_3-C_6$ alkynyl; phenyl, $C_6-C_{20}$ alkylaryl or $C_6-C_{20}$ aralkyl, wherein the phenyl nucleus is unsubstituted or substituted by one to three groups selected from the group consisting of halogen, $C_1-C_4$ alkyl, $C_1-C_4$ alkoxy, $C_1-C_4$ haloalkyl, nitro or cyano; or $R_3$ and $R_4$, together with the nitrogen atom to which they are attached, form a 5- or 6-membered heterocyclic ring system which may contain an additional oxygen or sulfur atom in the ring; and salts thereof, said process comprising the step of rearrangement of the corresponding enol ester, wherein said rearrangement is conducted in the presence of a alkali metal azide.

In the above definitions the alkyl radicals comprise both straight chain and branched radicals, e.g. methyl, ethyl, propyl, isopropyl, butyl, isobutyl, sec-butyl, tert-butyl, as well as all stereoisomers of the higher carbon number radicals. Alkenyl and alkynyl also comprise straight chain and branched radicals, e.g. vinyl, allyl, methallyl, butenyl, methylbutenyl and dimethylbutenyl, ethynyl, propynyl, butynyl, methylbutynyl and dimethylbutynyl, as well as all stereoisomers of the higher carbon number radicals.

By "cycloalkyl" is meant a group that encompasses cyclopropyl, cyclobutyl, cyclopentyl and cyclohexyl.

By "aryl" is meant either a non-heteroaromatic ring system or heteroaromatic ring system. By "alkylaryl" is meant an aryl group substituted by one or more alkyl groups. By "aralkyl" is meant an alkyl group substituted by one or more aryl groups.

Halogen is fluorine, chlorine, bromine or iodine.

A 5- or 6-membered heterocyclic ring system $-NR_3R_4$ which may contain an additional oxygen or sulfur atom in the ring includes aromatic and non-aromatic ring systems and for example includes pyrrole, pyrolidine, pyridine, piperidine, morpholine or thiomorpholine. These rings may also be substituted for example by one to three groups selected from the group consisting of halogen, $C_1-C_4$ alkyl, $C_1-C_4$ alkoxy, $C_1-C_4$ haloalkyl, nitro or cyano The cyclohexanedione derivatives of the formula I have good herbicidal and plant growth regulating properties.

Tautomerism is a type of isomerism in which migration of a hydrogen atom results in two or more structures, called tautomers. The cyclohexanedione derivatives of formula I can be obtained in different tautomeric forms. For example, methyl 4-propanoyl-3,5-cyclohexanedione-1-carboxylate can be obtained in the tautomer form of methyl 4-(propyl-1-hydroxymethylidene)-3,5-cyclohexanedione-1-carboxylate as well as other tautomer forms (see for example Tautomerism Scheme below):

a catalyst alone or additionally as a base reagent. When the alkali metal azide functions as a catalyst it is necessary to use an additional base reagent. The alkali metal azide may also be employed in sufficient quantities so that it additionally serves a base reagent for the process. In either case a phase-transfer catalyst may be used to enhance the reactivity of the alkali metal azide catalyst/base. It is to be expected that under certain conditions cation exchange may occur so that the actual catalytic or reagent azide species that facili- Tautomerism Scheme :

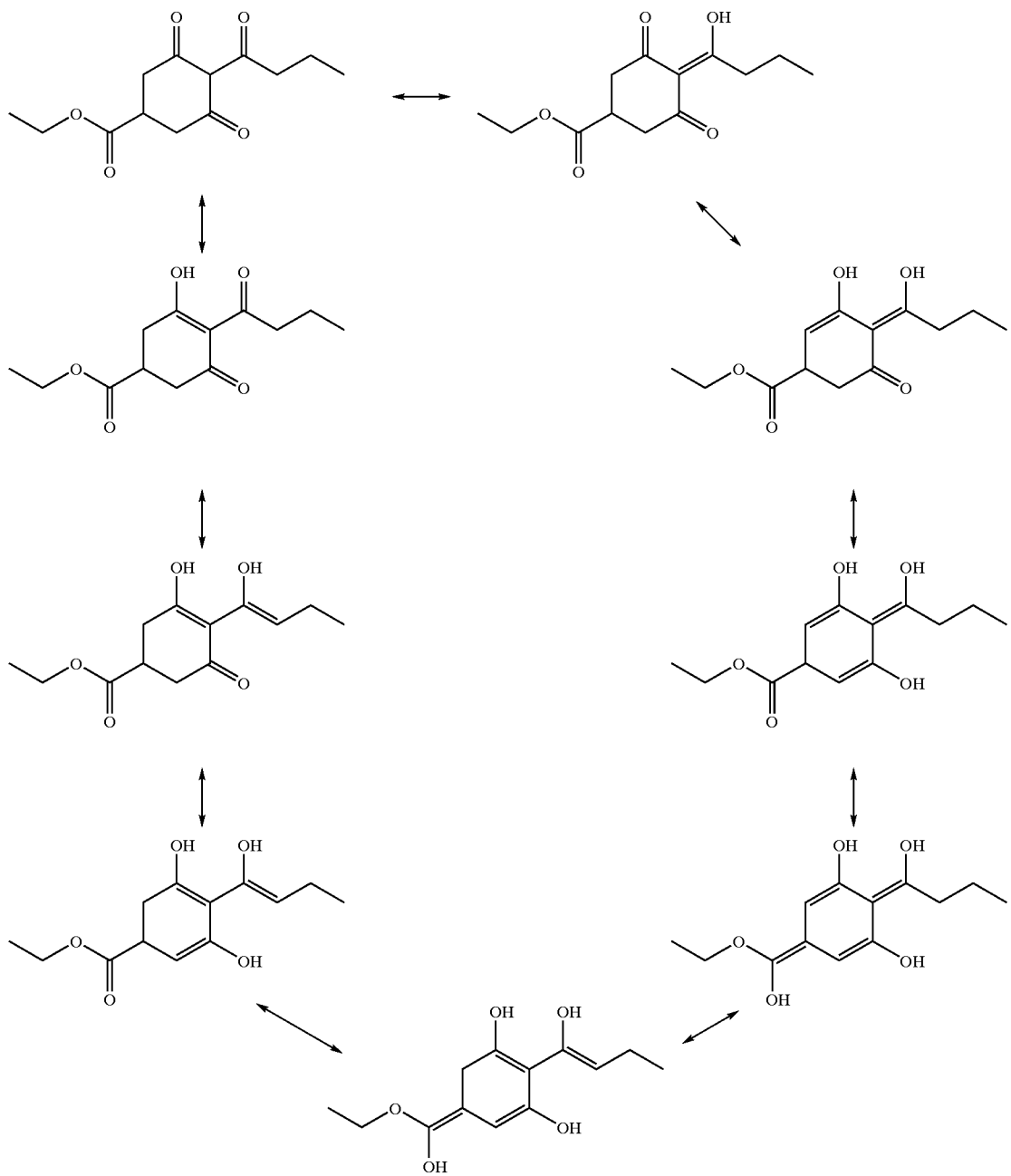

The alkali metal azide used in the instant process for preparing the cyclohexanediones of formula I include for example lithium azide, sodium azide, potassium azide and cesium azide. The alkali metal azide may function either as a tates the rearrangement reaction is an azide with a different counter cation.

The scope of the invention disclosed herein should not be construed to be limited by any particular chemical theory relating to the complexation, equilibration, reaction or acid-base chemistry of the components used to make the final product.

Suitable phase-transfer catalysts that may be employed in the instant process include complexing agents which solubilize cations in non-polar solvents (e.g. crown ethers such as 18-crown-6). The phase-transfer catalysts may be employed to increase the reaction rate of the rearrangement or otherwise reduce the energy input or quantity of reagents necessary to drive the reaction to completion. Whether a phase-transfer catalyst is used will depend a cost/benefit analysis for the given circumstances and the desired process design parameters (e.g. solvent systems, temperature reaction time etc.).

The preferred amount of alkali metal azide catalyst used in the process ranges from about 5 to 20 mole % relative to the enol ester. However, more alkali metal azide may be used, particularly if the azide is functioning as a reagent base.

The rearrangement process of this invention may be carried out in the presence of a solvent system. Suitable solvents for the rearrangement of the appropriate enol ester to the cyclohexanediones of formula I are for example toluene, DMF, acetone acetonitrile or other similar solvent systems. The solvent system may be extended to include other conventional solvents depending on whether a phase-transfer catalyst is used.

Suitable bases that may be used in the process are organic bases. Preferable organic bases include alkylamines such as trialkylamines or other functionally equivalent bases. Under the appropriate conditions it may be desirable to use for example ammonia or ammonium hydroxide as the base reagent or other similar base reagents. The trialkylamines are preferably tri(lower alkyl)amines having from 1 to 6, preferably 1 to 4 carbon atoms per alkyl group. A particularly preferable amine is triethylamine. Again, it is important to note that alkali metal azides or other salts may also be used as a suitable base reagent.

The base is used in an amount of from about 1 to about 4 moles per mole of enol ester, preferably 1 to 2 moles per mole of enol ester.

The temperatures used in the process will be limited to some extent by the solvent system used unless the rearrangement is conducted under pressure conditions. Generally, the suitable temperature conditions for the rearrangement are from about 20° C. to about 75° C. Reaction times can be short (i.e. on the order of minutes) or can be long (on the order of days) depending on the catalysts and the process design parameters used. Reaction times for a batch process run at room temperature typically ranges from 1 to 24 hours. Shorter reaction times and lower reaction temperatures may be preferable to avoid effects of undesirable side reactions and decomposition of reagents or catalyst.

Product yield may be improved by employing substantially anhydrous conditions in the process in order to avoid saponification of the enol-ester. Preferably, the rearrangement of the enol ester is conducted in the absence of water.

"Substantially anhydrous conditions" is defined as conditions sufficient to conduct the rearrangement reaction of the enol ester to the corresponding cyclohexanediones of formula I without an undesirable decrease in the efficiency of the process while taking into account the costs and benefits of obtaining the appropriate reagents and reactor design.

The cyclic enol ester starting materials that may be used in the invention include those disclosed in U.S Pat. Nos. 4,693,745 and 4,695,673 which are hereby incorporated by reference thereto in their entirety. The enol ester starting materials may be prepared by known procedures or otherwise may be prepared using conventional chemistry knowledge and the appropriate commercially available ultimate starting materials (e.g. methyl acetoacetate; see Yoshimoto et al. CHEMTECH (1989), 19(7), p. 431–4)(see U.S. Pat. Nos. 4,693,745 and 4,695,673). The alkali metal azide catalysts/reagents, base reagents, and phase-transfer catalysts are commercially available, may be prepared by known procedures or may otherwise may be prepared using conventional chemistry knowledge. For example, sodium azide is a commercially available azide catalyst/reagent. Similarly, 18-crown-6 is a commercially available phase-transfer catalyst.

The preferred enol ester starting materials used in the instant invention have the formula II:

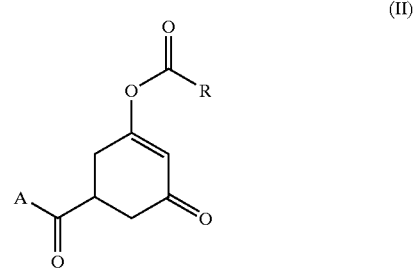

(II)

wherein the variables are as defined above for formula I. The salts, stereoisomers and tautomers of the compounds of formula II are also suitable starting materials. The salts of the compounds of formula II may be obtained by treatment of the compounds of formula II with the appropriate base. Suitable bases for obtaining the salts are preferably alkali metal hydroxides, alkaline earth metal hydroxides, iron, copper, nickel and zinc hydroxides, and also ammonia or quaternary $C_1$–$C_4$ alkylammonium or $C_1$–$C_4$ hydroxyalkylammonium bases.

The following examples illustrate further some of the specific features of the invention but are not intended to limit its scope. Where not otherwise specified throughout this specification and claims, temperatures are given in degrees centigrade.

EXAMPLE 1

Preparation of ethyl 2-cyclopropanoyl-1,3-cyclohexanedione-5-carboxylate

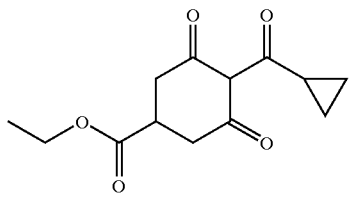

The appropriate O-acyl enol ester (25 g, 0.1 Mole) (obtainable from O-acylation of ethyl 1,3-cyclohexanedione-5-carboxylate with cyclopropanoyl chloride), triethylamine (13.4 g, 0.13 Mole), dimethylformamide (2 g, 0.02 Mole), and toluene (3.5 g, 0.04 mole) and sodium azide (0.65 g, 0.01 mole) are charged to a 200 ml round bottomed flask. The flask is equipped for reflux with a water cooled condenser, and agitated. The flask is heated in an oil bath to 55° C. for 3 hours. The rearranged product is extracted as a TEA salt, followed by acidification with hydrochloric acid in the presence of toluene. The product/toluene phase is separated, and the solvent is removed by evaporation to obtain ethyl 2-cyclopropanoyl-1,3-cyclohexanedione-5-carboxylate as a crude oil (17.6 g viscous oil, crude yield 70%).

EXAMPLE 2

Preparation of ethyl 2-aceto-1,3-cyclohexanedione-5-carboxylate

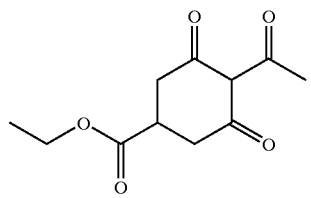

A round bottomed flask is charged with appropriate O-Acyl enol ester (15g, 0.066 mole)(obtainable from the acylation of ethyl cyclohexane-1,3-dione-5 carboxylate with acetyl chloride). The flask is equipped for stirring and sodium azide (0.52 g, 0.008 mole), DMF (1.6 g), toluene (2.8 g), and TEA (10.7 g, 0.105 mole) are added thereto. The flask is heated in an oil bath to 45° C. whereupon an exotherm raises the reaction temperature to 60° C. The mixture is cooled to 30° C. and is maintained for 1 hour without application of external heating. The reaction mixture was added to 100 ml water and the aqueous phase is separated and mixed with 20 ml toluene. The solution is then acidified with HCl to pH<2. The toluene phase is separated and the aqueous acid is back-extracted with dichloromethane. The solvent is removed from the combined organic extracts by rotary evaporation to obtain ethyl 2-aceto-1,3-cyclohexanedione-5-carboxylate product (9.6 g of a viscous oil crude yield 64%).

EXAMPLE 3

Preparation of ethyl 2-(3,5-dinitrobenzoyl)-1,3-cyclohexanedione-5-carboxylate

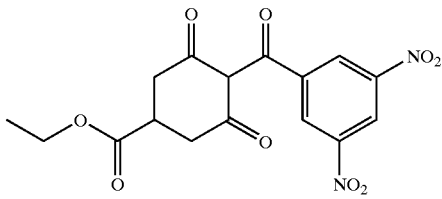

A round bottomed flask is charged with appropriate O-Acyl enol ester (15 g, 0.0396 mole)(obtainable from the acylation of ethyl cyclohexane-1,3-dione-5 carboxylate with 3,5-dinitrobenzoylchloride). The flask is equipped for stirring and sodium azide (0.26 g, 0.004 mole), DMF (1 g), toluene (5 g), and TEA (4.2 g, 0.041 mole) were added thereto. The flask was heated in an oil bath to 45° C. The disappearance of starting material was monitored by GC. Once the reaction is complete, water (48.6 ml) and toluene (7 g) is added to the reaction mixture followed by chilled to <10°. After separation the organic phase was extracted once with 8 ml of water. The combined aqueous extracts are back-extracted twice with toluene (2×5.4 g) whereby the first aqueous/organic solution is first acidified as in Example 2. The product containing organic phases are combined and washed with sodium bicarbonate. The organic solvent is removed by rotary evaporation to obtain ethyl 2-(3,5-dinitrobenzoyl)-1,3-cyclohexanedione-5-carboxylate product (9.6 g of a viscous oil, crude yield 64%).

The synthetic transformations described in the examples above were conducted under anhydrous or substantially anhydrous conditions. A crude product yield in the examples refers to the quantity of isolated material in comparison with the theoretical quantity that the starting enol ester could give. DMF=dimethyl formamide. 18-crown-6=1,4,7,10,13,16-hexaoxacyclooctadecane. TEA=triethylamine.

In summary, it is seen that this invention greatly simplifies the process for preparing cyclic 1,3-dicarbonyl compounds. This is achieved by using an azide catalyst/reagent system in a process for rearranging the corresponding enol esters. The use of the azide catalyst/reagent simplifies work-up and treatment of waste streams derived from the process. The instant invention avoids the costs and toxicity associated with the use of cyanide type catalysts/reagents. Variations may be made in proportions, procedures and materials without departing from the scope of the invention as defined by the following claims.

What is claimed is:

1. A process for preparing an acylated cyclical 1,3-dicarbonyl compound or tautomers thereof, comprising the step of rearrangement of the corresponding enol ester, wherein said rearrangement is conducted in the presence of an alkali metal azide.

2. A process according to claim 1, wherein said rearrangement is conducted in the presence of either
   (a) a catalytic amount of an alkali metal azide and a molar excess, with respect to the enol ester, of a base; or
   (b) a stoichiometric amount, with respect to the enol ester, of an alkali metal azide and a catalytic amount of a phase-transfer catalyst.

3. A process according to claim 2, wherein the enol ester has the formula:

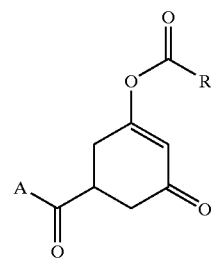

and salts and tautomers thereof, wherein
R is a group $C_1$–$C_{10}$ alkyl, $C_3$–$C_6$ cycloalkyl or phenyl, wherein the phenyl nucleus is unsubstituted or substituted by one to three groups selected from the group consisting of halogen, $C_1$–$C_4$ alkyl, $C_1$–$C_4$ alkoxy, $C_1$–$C_4$ haloalkyl, nitro or cyano;
A is —$OR_2$, —$SR_2$ or —$NR_3R_4$ radical;
$R_2$, $R_3$ and $R_4$ are each independently, hydrogen, $C_1$–$C_6$ alkyl, $C_1C_6$ haloalkyl, $C_2$–$C_{10}$ alkoxyalkyl, $C_2$–$C_{10}$ alkylthioalkyl; $C_3$–$C_6$ alkenyl which is unsubstituted or substituted by halogen, $C_1$–$C_4$ alkoxy or $C_1$–$C_4$ alkylthio; $C_3$–$C_6$ alkynyl; phenyl, $C_6$–$C_{20}$ alkylaryl or $C_6$–$C_{20}$ aralkyl, wherein the phenyl nucleus is unsubstituted or substituted by one to three groups selected from the group consisting of halogen, $C_1$–$C_4$ alkyl, $C_1$–$C_4$ alkoxy, $C_1$–$C_4$ haloalkyl, nitro or cyano; or $R_3$ and $R_4$, together with the nitrogen atom to which they are attached, form a 5- or 6-membered heterocyclic ring system which may contain an additional oxygen or sulfur atom in the ring; and salts thereof.

4. A process according to claim 1, wherein the acylated cyclic 1,3-dicarbonyl compounds prepared have the formula:

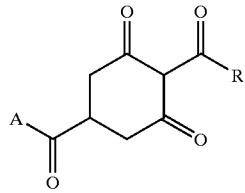

and salts and tautomers thereof, wherein the variable substituents are as defined above.

5. A process according to claim 1, wherein the alkali metal azide is sodium azide.

6. A process according to claim 1, wherein the process is conduced in the presence of a base.

7. A process according to claim 1, wherein said base is triethylamine.

8. A process according to claim 1, wherein the process is conduced in the presence of a solvent.

9. A process according to claim 7, wherein the solvent is toluene.

* * * * *